United States Patent [19]

Miller, Jr.

[11] Patent Number: 5,456,913
[45] Date of Patent: Oct. 10, 1995

[54] METHOD FOR TREATING ANIMALS INFESTED WITH ECTOPARASITES

[75] Inventor: Gordon G. Miller, Jr., Washington, D.C.

[73] Assignee: Safety Pet Products Inc., Richmond, Va.

[21] Appl. No.: 286,919

[22] Filed: Aug. 8, 1994

Related U.S. Application Data

[63] Continuation-in-part of Ser. No. 142,799, Oct. 25, 1993, abandoned.

[51] Int. Cl.$^6$ .......................... A01N 65/00; A01N 59/10; A01N 59/08; A01K 29/00
[52] U.S. Cl. ...................... 424/195.1; 424/676; 424/680; 119/158; 514/876; 514/919
[58] Field of Search .................... 424/195.1, 680, 424/676, DIG. 10; 514/919, 876; 119/158

[56] References Cited

U.S. PATENT DOCUMENTS

| | | | |
|---|---|---|---|
| 4,193,986 | 3/1980 | Cox | 424/195.1 |
| 4,342,743 | 8/1982 | Panton-Moor | 424/61 |
| 4,374,853 | 2/1983 | Workman | 514/506 |
| 4,379,168 | 4/1983 | Dotolo | 514/763 |
| 4,668,434 | 5/1987 | Bowman | 252/522 |
| 4,808,615 | 1/1989 | Ott et al. | 514/89 |
| 4,874,752 | 10/1989 | Baker | 514/89 |
| 4,935,248 | 6/1990 | Witkin | 424/616 |
| 4,973,589 | 11/1990 | Barnett | 514/245 |
| 5,017,615 | 5/1991 | Workman | 514/560 |
| 5,066,497 | 11/1991 | Witkin | 514/616 |
| 5,084,281 | 1/1992 | Dillon | 424/677 |
| 5,194,264 | 3/1993 | Van Tonder | 424/405 |
| 5,221,535 | 6/1993 | Domb | 424/417 |

*Primary Examiner*—John W. Rollins
*Attorney, Agent, or Firm*—Leydig, Voit & Mayer, Ltd.

[57] ABSTRACT

Methods for treating animals infested with ectoparasites are provided for. The methods comprise providing a solution consisting essentially of water and sea salt. The solution preferably includes a dissolved skin conditioner, preferably a natural skin conditioner, such as oat grains. The solution is applied to any animal, by dipping, spraying or in an aqueous-based carrier such as a shampoo, in an amount and for a period of time sufficient to deinfest the animal.

13 Claims, No Drawings

METHOD FOR TREATING ANIMALS INFESTED WITH ECTOPARASITES

This is a continuation-in-part of application Ser. No. 08/142,799 filed on Oct. 25, 1993, now abandoned.

FIELD OF THE INVENTION

This invention relates to compositions and methods useful for treating animals which are infested with fleas, ticks, and other ectoparasites, and in particular, to such compositions which comprise natural, nontoxic ingredients.

BACKGROUND OF THE INVENTION

The problems associated with animals such as pets which are infested with fleas, ticks, and other ectoparasites are well known. There are a wide variety of dips, sprays, powders, shampoos, collars, and the like which are designed to rid animals of such pests. Many are effective. Many such methods, however, rely on synthetic or toxic ingredients which may present a potential hazard to a pet, a pet owner, or to the environment. Further, existing treatments may contain relatively expensive ingredients and may require careful formulation and application to achieve satisfactory results while avoiding potentially harmful effects.

It is an object of the subject invention, therefore, to provide a composition which is effective in treating animals infested with ectoparasites, but which also is composed of natural, nontoxic ingredients which are safe to a pet, a pet owner, and to the environment. Another object of the subject invention is to provide such compositions which incorporate inexpensive ingredients which are easily formulated, packaged, and applied.

Those and other objects and advantages of the present invention will be apparent from the following description.

SUMMARY OF THE INVENTION

The subject invention is based on applicant's observation that a solution of sea salt is effective in ridding animals of fleas and ticks. Accordingly, the invention provides for a method of treating animals infested with ectoparasites. The method comprises providing a solution consisting essentially of water and sea salt. The solution preferably includes a dissolved skin conditioner, preferably a natural skin conditioner, such as oat grains. The solution then is applied to the animal, such as by dipping, spraying or with an aqueous-based carrier, in an amount and for a period of time sufficient to deinfest the animal.

It will be appreciated, therefore, that the methods and composition of the subject invention not only are effective in deinfesting an animal, but that the compositions are composed essentially of natural ingredients which are safe to pets and humans and pose little risk to the environment, especially as compared to many synthetic chemical-based treatments.

DETAILED DESCRIPTION OF THE INVENTION

The compositions and methods of the subject invention utilize sea salt to deinfest an animal carrying ectoparasites. Sea salt is produced by evaporation or from mining of deposits and is commercially available from many sources, e.g., for use in home aquariums. In general, commercial grade sea salt may be used in the subject invention. Although the reasons for this are not fully understood, however, it has been observed that sea salt obtained from CARGILL Salt Division, P.O. Box 5621, Minneapolis, Minn. 55440 or CARGILL Leslie Salt Co., 7220 Central Avenue, Newark, Calif. 94560-4206, is particularly effective.

The sea salt is dissolved in water for application to an animal. Accordingly, the sea salt is provided in a form which will facilitate its dissolution into water, such as finely divided crystals. Because salt is highly soluble in water, however, the size of the salt crystals is not critical. The water also may be heated slightly to facilitate dissolution, especially if the sea salt is not finely divided. Further, as discussed below, it may be advantageous to pelletize the salt.

The sea salt will be dissolved in water in concentrations sufficient to deinfest an animal. By deinfest, it is meant simply that the ectoparasites are either killed, incapacitated, or otherwise driven off an animal. It is expected that sea salt in a concentration of about 1 cup per from about 10 to about 16 gallons of water will be effective. It will be appreciated, however, that the optimum amount will vary somewhat, for example, depending on the inherent efficacy of a particular grade of sea salt.

Likewise, the animal will be treated for a time sufficient to allow deinfestation of the animal. In general, this will require treatment for about 5 to about 20 minutes. The precise time of treatment, however, may vary somewhat. More concentrated solutions will require shorter treatment times. More heavily infested animals may require longer treatment times.

The sea salt solution may be applied by any other suitable method, such as spraying or with an aqueous-based carrier. Because an animal must be exposed to the solution for a significant period of time, during which the animal may be inclined to shake off the solution, however, dipping the animal in a bath of the sea salt solution is preferred. Preferably the temperature of the bath will be comfortable to the animal, but otherwise, the temperature is not believed to be critical.

Preferably, the sea salt solution also includes a conditioner to minimize drying of an animal's skin which otherwise might occur as a consequence of frequent bathing. Preferably, the skin conditioner is a dry, water-soluble natural ingredient, such as oat grains. Such conditioners preferably are finely ground to facilitate their dissolution in water. Many other water-soluble conditioners are known, however, and in general may be used in the subject invention.

The amount of skin conditioner incorporated in the sea salt solution can vary greatly. Preferably, there is an amount sufficient to compensate for drying of an animal's skin which may be caused by frequent bathing. On the other hand, little benefits will be obtained by using excessively large amount of skin conditioner. For example, when oat grains and the like are used as a skin conditioner, it is expected that one part conditioner per from about 6 to about 9 parts of sea salt would provide satisfactory results.

The sea salt, along with any desired skin conditioner, preferably is compounded and packaged in a dry state for mixing with water immediately prior to use by a consumer. The sea salt and skin conditioner, however, can be packaged as a liquid concentrate. The sea salt, and any added skin conditioner, also can be pelletized, with binders if necessary, for example, in a pellet of a predetermined quantity sufficient for a single bath.

It will be appreciated, therefore, that the novel solutions may be easily formulated and applied. The ingredients are easily handled and shipped, especially if packaged as a dry concentrate for mixing immediately prior to use. The concentrate can be easily mixed with water by a consumer. The concentrate will be effective in solutions having a relatively wide range of concentrations, giving a consumer a wide margin of error in mixing a bath. Sea salt also is very inexpensive and is nontoxic.

The novel compositions and methods also may be applied with an aqueous-based carrier that will keep the sea salt solution in contact with the skin of the animal for a sufficient time to destroy the fleas and ticks. This approach is particularly desirable where it may be impractical to dip such as with larger animals. For example, the aqueous-based carrier can be a conventional liquid shampoo so that an infested animal may be treated and cleaned at the same time. The shampoo can be any of the conventional aqueous-based formulations as are commonly used to bathe and clean animals. In general, a formulation of shampoo and sea salt should comprise at least 5 wt % sea salt, and approximately 50 wt % sea salt is recommended. The precise amount of sea salt, however is subject to considerable variation depending on the balance of cleaning and deinfestation properties desired and the effectiveness of the sea salt used. Such formulations, if necessary or desired, also may include conditioner, either included in the shampoo as in common or as an added ingredient. If added, the conditioner can include those discussed above such as finely ground oat grains, and can be added in amounts relative to sea salt as described herein. For example, a mixture of equal parts commercial aqueous based shampoo and a 95/5 wt % admixture of sea salt and ground oat grains is expected to provide satisfactory results.

Preferably, when the novel compositions incorporate shampoo, they are lathered into the animal and rinsed therefrom as with conventional shampoos, except of course that the shampoo is left on the animal for a time sufficient to deinfest it. Shampoo formulations, however, may be incorporated in baths as well.

It will also be appreciated that aqueous-based gels or cremes could be used to suspend the sea salt solution so as to keep it on the animal for an effective time before rinsing off.

The invention is further described by reference to the following example. It is not intended to limit the scope of the invention; rather, it is presented merely to facilitate the practice of the invention by those of ordinary skill in the art and to further disclose the inventor's best mode of doing so.

EXAMPLE 1

A dry mixture of 95 wt % sea salt (obtained from Cargill Leslie Salt Co.) and 5 wt % finely ground oat grains was compounded together. One-half cup of the dry mixture was dissolved in eight gallons of water to produce a bath.

Flea and tick infested dogs were treated by dipping them in the bath for from about 5 to about 10 minutes. It was observed that within approximately 5–8 minutes that the fleas and ticks began to appear to become bloated and to float to the surface of the bath. The fleas and ticks eventually were killed, some apparently having burst, and sank to the bottom of the bath. After the treatment, the animals were observed to be substantially free from ticks and fleas.

This invention has been disclosed and discussed primarily in terms of specific embodiments thereof, but it is not intended to be limited thereto. Other modifications and embodiments will be apparent to workers in the art.

I claim as my invention:

1. A method of treating animals infested with ectoparasites, the method comprising:

providing a solution consisting essentially of water and sea salt; and applying the solution to an infested animal in an amount and for a period of time sufficient to deinfest the animal.

2. The method of claim 1, wherein the solution comprises about 1 cup sea salt per from about 10 to about 16 gallons of water.

3. A method of claim 1, wherein the solution further includes a skin conditioner.

4. The method of claim 3, wherein the skin conditioner is ground oat grains.

5. The method of claim 3, wherein the skin conditioner is present in an amount equal to 1 weight part per from about 6 to about 9 weight parts sea salt.

6. The method of claim 1, wherein the solution further comprises an aqueous based shampoo.

7. The method of claim 1, wherein the method comprises dipping an infested animal into a bath of the solution.

8. A method of treating and cleaning animals infested with ectoparasites, the method comprising:

providing a formulation consisting essentially of a sea salt and aqueous based shampoo; and applying the formulation to an infested animal in an amount and for a period of time sufficient to deinfest and clean the animal.

9. The method of claim 8, wherein the formulation comprises at least about 5 wt % sea salt.

10. The method of claim 8, wherein the formulation further includes a skin conditioner.

11. The method of claim 10, wherein the skin conditioner is ground oat grains.

12. The method of claim 10, wherein the skin condition is present in an amount equal to 1 weight part per about 6 to about 9 weight parts sea salt.

13. The method of claim 8, wherein the method further includes diluting the formulation with water.

* * * * *